(12) United States Patent
Zhou

(10) Patent No.: US 12,392,512 B2
(45) Date of Patent: Aug. 19, 2025

(54) AIR STERILIZATION DEVICE WITH HEATING APPARATUS

(71) Applicant: Guangzhou T.K Medical Instrument Co., Ltd., Guangzhou (CN)

(72) Inventor: Xing Zhou, Guangzhou (CN)

(73) Assignee: GUANGZHOU T.K MEDICAL INSTRUMENT CO., LTD., Guangdong (CN)

(*) Notice: Subject to any disclaimer, the term of this patent is extended or adjusted under 35 U.S.C. 154(b) by 581 days.

(21) Appl. No.: 17/878,797

(22) Filed: Aug. 1, 2022

(65) Prior Publication Data

US 2022/0373203 A1 Nov. 24, 2022

Related U.S. Application Data

(63) Continuation of application No. PCT/CN2020/141178, filed on Dec. 30, 2020.

(51) Int. Cl.
*A61L 9/20* (2006.01)
*F24F 5/00* (2006.01)
(Continued)

(52) U.S. Cl.
CPC .................. *F24F 8/22* (2021.01); *A61L 9/20* (2013.01); *F24F 5/0042* (2013.01); *F24F 8/133* (2021.01);
(Continued)

(58) Field of Classification Search
CPC ............ F24F 8/22; F24F 8/133; F24F 5/0042; F24H 3/002; A61L 9/20; A61L 2209/11; A61L 2209/14
See application file for complete search history.

(56) References Cited

U.S. PATENT DOCUMENTS 5,330,722 A * 7/1994 Pick .................. A61L 9/16
250/492.1
5,675,401 A 10/1997 Wangler et al.
(Continued)

FOREIGN PATENT DOCUMENTS

CN 2369689 Y 3/2000
CN 1465404 A 1/2004
(Continued)

OTHER PUBLICATIONS

Guangzhou T.K. Medical Instrument Co., Ltd., PCT/CN2020/141178, International Search Report and Written Opinion, Mar. 29, 2021, 17 pgs.
(Continued)

*Primary Examiner* — Sean M Luck
(74) *Attorney, Agent, or Firm* — Morgan, Lewis & Bockius LLP

(57) ABSTRACT

The air sterilization device with heating apparatus comprises a mainframe, a sterilization system, a heating system, circuits and a control system and a housing. The sterilization system includes an ultraviolet sterilization apparatus to sterilize and disinfect air; the heating system heats the air to inactivate virus; and the housing has an air inlet and an air outlet. Air can circulate into the housing through the air inlet with the action of mainframe and then the air is discharged from the air outlet into a room after the disinfection and sterilization processes are finished. The device with heating apparatus aims at the secondary inactivation of viruses by high temperature after the sterilization and disinfection processes are finished by ultraviolet sterilization apparatus and heating system, and at the decomposition of ozone produced in the process of ultraviolet disinfection to eliminate secondary air pollution by ozone.

20 Claims, 11 Drawing Sheets

Figure 1:
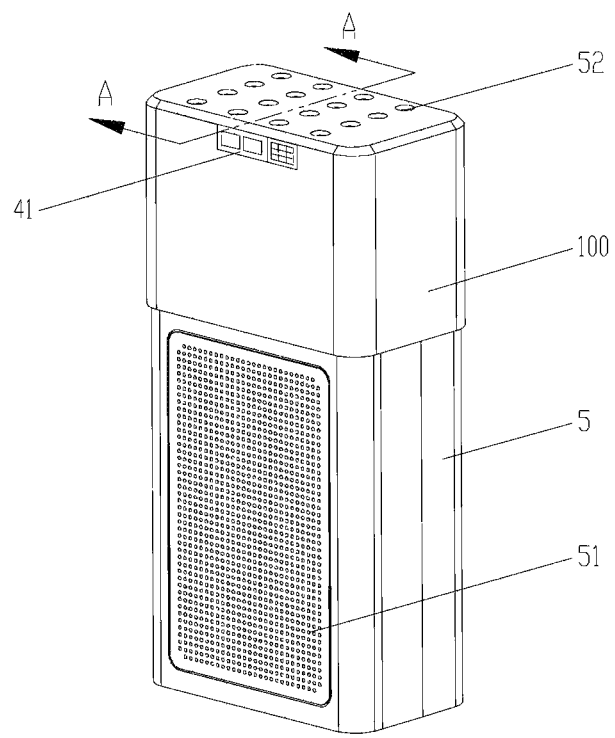
Figure 1:
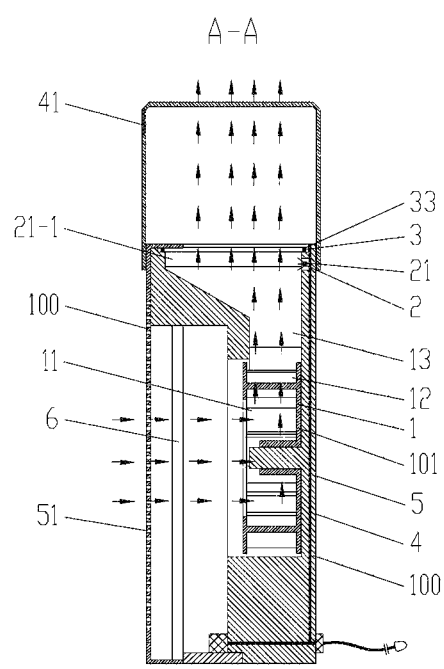

(51) Int. Cl.
*F24F 8/133* (2021.01)
*F24F 8/22* (2021.01)
*F24H 3/00* (2022.01)

(52) U.S. Cl.
CPC .......... *F24H 3/002* (2013.01); *A61L 2209/11* (2013.01); *A61L 2209/14* (2013.01)

(56) References Cited

U.S. PATENT DOCUMENTS

| | | | |
|---|---|---|---|
| 2004/0120845 | A1* | 6/2004 | Potember .................. A61L 9/20 422/123 |
| 2005/0129571 | A1* | 6/2005 | Centanni ................. A61L 2/202 422/62 |
| 2005/0201206 | A1 | 9/2005 | Luc |
| 2006/0146384 | A1 | 7/2006 | Schultz et al. |
| 2012/0140240 | A1 | 6/2012 | Hillman et al. |
| 2013/0301033 | A1 | 11/2013 | Alarousu et al. |
| 2014/0327960 | A1 | 11/2014 | Yoshida et al. |
| 2018/0021471 | A1* | 1/2018 | Krosney .............. B01D 53/007 422/4 |

FOREIGN PATENT DOCUMENTS

| | | |
|---|---|---|
| CN | 201818521 U | 5/2011 |
| CN | 103135369 A | 6/2013 |
| CN | 103163154 B | 6/2013 |
| CN | 103424880 A | 12/2013 |
| CN | 103941403 A | 7/2014 |
| CN | 107861230 A | 3/2018 |
| CN | 108413867 A | 8/2018 |
| CN | 108490597 A | 9/2018 |
| CN | 109059100 A | 12/2018 |
| CN | 109187491 A | 1/2019 |
| CN | 109470710 A | 3/2019 |
| CN | 109470711 A | 3/2019 |
| CN | 109490201 A | 3/2019 |
| CN | 109580640 A | 4/2019 |
| CN | 109916909 A | 6/2019 |
| CN | 111239154 A | 6/2020 |
| CN | 211751295 U | 10/2020 |
| CN | 215607953 U | 1/2022 |
| EP | 1992905 A1 | 11/2008 |
| FR | 2864438 A1 | 7/2005 |
| GB | 1285203 A | 8/1972 |
| JP | H04208913 A | 7/1992 |
| JP | H07281098 A | 10/1995 |
| JP | H1195113 A | 4/1999 |
| JP | 2005342509 A | 12/2005 |
| JP | 2007121749 A | 5/2007 |
| WO | WO1981003704 A1 | 12/1981 |
| WO | WO1998014132 A1 | 4/1998 |
| WO | WO2012127880 A1 | 9/2012 |
| WO | WO2013089258 A1 | 6/2013 |

OTHER PUBLICATIONS

Guangzhou T.K. Medical Instrument Co., Ltd., PCT/CN2020/141178, International Preliminary Report on Patentability, Jul. 19, 2021, 5 pgs.

Feng Zhengde et al., "Shaped ring light differential confocal measurement with high spatial resolution", Applied Optics, vol. 28, No. 4, Jul. 31, 2007 (Jul. 31, 2007), 10 pgs.

Guangzhou T.K. Medical Instrument Co., Ltd., EP20962322, Partial European Search Report, Oct. 18, 2024, 11 pgs.

Guangzhou T.K. Medical Instrument Co., Ltd., EP20962322, Supplementary European Search Report, Jan. 14, 2025, 10 pgs.

Guangzhou T.K. Medical Instrument Co., Ltd., CN202011325286, First Office Action, Oct. 25, 2024, 19 pgs.

Guangzhou T.K. Medical Instrument Co., Ltd., CN202011325286, Second Office Action, Feb. 19, 2025, 18 pgs.

* cited by examiner

AIR STERILIZATION DEVICE WITH HEATING APPARATUS

CROSS-REFERENCE TO RELATED APPLICATION

This application is a continuation of PCT Application No. PCT/CN2020/141176, filed on Dec. 30, 2020, which claims the benefit of and priority to Chinese Patent Application No. 202011325286.2, filed on Nov. 23, 2020 with State Intellectual Property Office of the People's Republic of China, the entire contents of which are incorporated herein by reference.

TECHNICAL FIELD

The disclosed implementations relate generally to an air sterilization system, and in particular, to an air sterilization system with heating apparatus.

BACKGROUND

Air has become a carrier of various kinds of pollutants, bacteria and viruses and has hidden effect on people's physical health, as the air is ever-increasingly polluted, in particular, in seasons with high incidence of infectious diseases such as flu, pneumonia. Therefore, air purification plays a very important role in daily life.

At present, the common means of air purification is to utilize air purifier to purify indoor air. The currently listed air purifiers usually constitute motor, fan and filter devices, motor and fan circulate indoor air and various kinds of pollutants are cleared away or absorbed by filter devices. In order to eliminate viruses existed in indoor air, the air purifiers are commonly installed with antibacterial devices, such as electrostatic screen, anion, plasma devices and ultraviolet sterilizers.

Ultraviolet sterilization apparatus and anion devices, inevitably produce ozone in the course of work, which brings secondary pollution to the air, thus requiring further improvement on the current air purifiers and disinfection devices.

SUMMARY

The present application is directed to an air sterilization device with heating apparatus, which is capable of sterilizing and disinfecting bacteria and viruses existed in air by ultraviolet sterilization apparatus first, and then heating the air at least to 56° C. (preferably above 60° C.) by the heating system to inactivate the viruses twice. At the same time, heating up the air can quickly eliminate and decompose the ozone produced in the course of ultraviolet disinfection, in a bid to disinfect and purify the air better.

The air sterilization device of the present application comprises: a mainframe, a sterilization system, a heating system, circuits, a control system and a housing, wherein:
  the sterilization system is an ultraviolet sterilization apparatus which can sterilize and disinfect the air;
  the heating system can heat the air to inactivate virus;
  the housing comprises air inlet and air outlet;
  the mainframe, the ultraviolet sterilization apparatus and the heating system connect power source through the circuits and control system; and
  the ultraviolet sterilization apparatus and the heating system are installed in a housing; and with the action of the mainframe, the air flows into the housing through the air inlet and is discharged from the air outlet into room after the air is sterilized and disinfected by the ultraviolet sterilization apparatus and the heating system.

The air inlet is located in the bottom of the housing and the air outlet on the top of the housing. After the device is powered, the mainframe works and air flows into the housing through the air inlet. Going forward, the ultraviolet sterilization apparatus sterilizes and disinfects the air and the heating system heats the air in order to inactivate viruses twice. To make sure inactivated effect, the heating system should be heated up to 60° C., which can decompose the ozone produced in the course sterilization by the ultraviolet sterilization apparatus into oxygen, so as to avoid secondary pollution and maximize the air sterilization and purification effect.

The circuits and control system can control the opening and closing of the mainframe, the ultraviolet sterilization apparatus and the heating system. The time of duration and the intensity of ultraviolet irradiation of the ultraviolet sterilization apparatus can be set and adjusted by the control panel of the circuits and control system. The heating temperature and heating duration of the heating system can be set and adjusted by the control panel of the circuits and control system.

The circuits and control system can be set to sterilize and disinfect the air intelligently. The time of duration and the intensity of ultraviolet irradiation of the ultraviolet sterilization apparatus and the heating temperature and heating duration of the heating system can be set. In addition, the device is installed with ultraviolet and temperature sensors, with ultraviolet disinfection and heating functions set in the meantime. Thus, the device can be controlled intelligently by the setting program.

The heating system can eliminate the ozone quickly generated in the course of sterilization and disinfection by the ultraviolet sterilization apparatus to reduce the ozone level of the air discharged into the room.

The mainframe is a centrifugal machine that includes an air inlet unit and an exhaust unit. When the centrifugal machine works, air is drawn in from the air inlet unit by the centrifugal machine and then discharged through the exhaust unit. The air circulates between a room and the housing.

The mainframe is a two-stage fan that includes a motor, a rotating shaft, a first-stage blade, a second-stage blade and a permanent seat.

The motor connects to the first-stage blade and the second-stage blade by the rotating shaft; the motor is installed in the permanent seat; the motor drives the first stage blade and the second stage blade to rotate by the rotating shaft and the circuits and control system. The first-stage blade and the second-stage blade can discharge the sterilized and disinfected air into the room through rotating.

The two-stage fan includes protective cap. The motor, the rotating shaft, the first stage blade, the second stage blade and the permanent seat are assembled and installed in the protective cap that provides good protection.

The first stage blade is smaller than the second stage blade in size, which can discharge the sterilized and purified air into the room in an efficient and quick way.

The heating system can be a heating rod and/or a heating plate and/or a heating coil. The heating system can use one of the above-mentioned heating methods or a combination of multiple heating methods. There various changes in form and details may be made therein without departing from the spirit and scope of the present application.

Furthermore, the heating coil is wound by heating wire along the direction of air flow and distributed longitudinally. This winding method along the direction of air flow can maximize the width of air heating distance, killing viruses and decompose ozone better.

The ultraviolet sterilization apparatus is installed in the ultraviolet disinfection chamber. Ultraviolet disinfection utilizes appropriate wavelength of ultraviolet rays to destroy DNA or RNA molecular structure of microbial body cells, resulting in growth cell death and/or regenerative cell death, to achieve the effect of sterilization and disinfection. Thus, ultraviolet rays may cause accidental harm to human body, if poorly protected in the course of sterilization. In addition to avoiding accidental harm to human body, it is imperative to install the ultraviolet sterilization apparatus in the ultraviolet disinfection chamber to screen ultraviolet rays.

The ultraviolet disinfection chamber is made of materials that are resistant to ultraviolet radiation and prevents the leakage of ultraviolet rays to guarantee the isolation effect of the ultraviolet disinfection chamber.

The ultraviolet disinfection chamber is made of mirror-surface stainless steel that can reflect ultraviolet rays, or minor-surface polymer materials that are resistant to ultraviolet radiation.

The ultraviolet disinfection chamber can enhance the ultraviolet intensity in it by the reflection of ultraviolet rays, and strengthen the sterilization effect.

The material, reflecting the ultraviolet rays, can enhance the ultraviolet intensity in the ultraviolet disinfection chamber, so that sterilization effect is better. To further strengthen the sterilization effect, multiple ultraviolet sterilization apparatuses, such as ultraviolet lamps, are installed evenly around the ultraviolet disinfection chamber, ensuring that the ultraviolet rays are evenly placed inside the said ultraviolet disinfection chamber to keep sterilization effect.

The heating system heats the air to inactivate viruses. The air temperature is no less than 56° C. and normally is set at 60° C. In most cases, capsid proteins of viruses denaturates at 55-60° C. within a few minutes, rendering the virus incapacitated. Thus, the temperature heated by the heating system is at above 56° C. or 60° C. to better inactivate viruses. At the same time, the ozone is discomposed quickly in the course of sterilization and disinfection by the ultraviolet sterilization apparatus when it is at above 50° C., in a bid to avoid the ozone produced in the sterilization process to cause secondary pollution to the air.

The air enters the housing through the air inlet, first passes through the ultraviolet sterilization apparatus, and next passes through the heating system to be disinfected, and then the sterilized air is discharged from the air outlet into the room. Normally, the air is first sterilized by the ultraviolet sterilization apparatus, and then heated by the heating system to inactivate the possible viruses in the air twice and to decompose the ozone produced by the ultraviolet sterilization apparatus and strengthen the sterilization effect of air.

The heating system and the ultraviolet sterilization apparatus are integrated into one piece.

The ultraviolet sterilization apparatus sterilizes the air in the ultraviolet disinfection chamber and at the same time the heating system heats the air sterilized by the ultraviolet sterilization apparatus.

The heating system not only strengthens the inactivation effect of viruses, but also heats the ozone generated in the process of disinfection and sterilization of the ultraviolet sterilization apparatus to accelerate the decomposition of the ozone.

The heating system heats the air sterilized by the ultraviolet sterilization apparatus and maintains the set temperature. The heating system is provided with a temperature setting device so that the heating temperature of the heating system is kept constant, and the best heating temperature can be set according to the needs of different sources of infection, to better ensure the inactivation effect of viruses.

The air sterilization device with heating apparatus comprises an air filtration apparatus that can filter dust particles, odor, toxic gases and other air pollutants in the air.

The air filtration apparatus is made of ceramic materials which can be heated at above 56° C. by the heating system. But the optimum temperature is at 70° C. to 150° C. The air passes by heated ceramic materials to kill bacteria and viruses. The air filtration apparatus is replaced regularly, which is safer and more sanitary, which can quickly kill bacteria and viruses attached to the ceramic materials at high temperature and which can improve the efficiency of air sterilization and disinfection.

The air sterilization device with heating apparatus comprises water filtration apparatus. Viruses usually require a carrier to spread. The greater the air fluctuates and the faster the viruses spread. The water filtration apparatus can screen the motion of the sterilized and disinfected air, so that the air is discharged into the room, avoiding large fluctuations in surrounding air, in a bid to slow down the movement of the viral vectors and the speed of viruses.

The water filtration apparatus is water curtain by which the sterilized air passes into the room or water bath that screens the air motion with water in it to discharge the air into the room. The water in the water bath can reduce the air fluctuations. And then the air is discharged into the room in a gentle manner.

The water bath comprises thermostat, which keeps the liquid in the water bath at a constant temperature. And according to different needs, different temperature can be set so as to better inactive viruses.

The heating unit in the thermostat is integrated with the heating system. The air sterilized by ultraviolet rays enters the water bath through pipelines. The liquid in the water bath is heated by the heating unit and inactivates the sterilized air to decompose the ozone produced in the course of ultraviolet disinfection and at the same time to discharge the air into the room at a very gentle speed to reduce air fluctuations.

The air booster pump is an installed exhaust pipe in the front of the water bath, which increases air pressure so as to ensure that the sterilized air flows into the water bath and it is discharged along the motion of liquid in the water bath.

The air sterilization device with heating apparatus comprises cooling apparatus that can reduce the temperature of the air heated by the heating system to avoid the damage to the air filtration apparatus or to cause accidental harms.

The cooling apparatus is the heat conduction cooling plate which is made of thermoelectric ceramics and includes a cooling surface and a heat delivery surface. The cooling surface is installed on the side toward the exhaust pipe and cools the air, and the heat delivery surface on the side toward the ultraviolet sterilization apparatus and conduct heat into the ultraviolet disinfection chamber. The air passes through the cooling surface, which works to reduce the temperature of the air to a safe temperature to prevent the air filtration apparatus from being damaged by high air temperature or prevent accidental damage. The heat delivery surface conducts the heat generated in the process of reducing air temperature to the side of the ultraviolet sterilization apparatus and assists heating system to heat the air disinfected by the ultraviolet sterilization apparatus. In practice, the cooling apparatus may be a cold rinse bank, cold water pipes or other cooling apparatus. It also will be understood by those of ordinary skill or technology in the art that various changes in form and details may be made therein without departing from the spirit and scope of the present application.

The housing is made of stainless steel material or high polymer material, which is easy for daily cleaning while the strength and the capacity to resist ultraviolet rays are guaranteed.

In practice, when the mainframe is powered on, air enters in the housing through the air inlet. The air enters into the mainframe through the air inlet unit after it is filtered by the air filtration apparatus. The air is discharged through the exhaust unit and enters into the ultraviolet disinfection chamber through the exhaust pipe. And then, the ultraviolet sterilization apparatus disinfects the air filtered and the heating system heats the air to inactivate viruses in the air and decompose the ozone produced in the course of ultraviolet disinfection in a quick manner. The sterilized air enters in the water bath through the exhaust pipe. The liquid in the water bath is heated by the heating rod and can screen the air motion, inactivate the possible residual viruses and decompose the residual ozone completely. The air is discharged gently into the room from the air outlet, avoiding causing fluctuations in surrounding air.

The air sterilization device with heating apparatus comprises mainframe, sterilization system, heating system, circuits and control system and housing. The sterilization system is the ultraviolet sterilization apparatus that can sterilize and disinfect air. The heating system heats the air to inactivate viruses. The housing comprises air inlet and air outlet. With the action of mainframe, air flows into the housing through air inlet and is discharged from the air outlet into room after the air is sterilized and disinfected through the ultraviolet sterilization apparatus and the heating system. The air sterilization device with heating apparatus can heat the air to inactivate viruses twice and decompose the ozone produced in the course of sterilization and disinfection by the ultraviolet sterilization apparatus and the heating system, so as to avoid secondary pollution to the air. The water filtration apparatus can screen the motion of the sterilized and disinfected air, so that the air can be discharged into room, avoiding large fluctuations in surrounding air, in a bid to slow down the movement of the viral vectors and the speed of viruses.

The air sterilization device with heating apparatus can be used not only to sterilize and disinfect indoor air, but also the air in various vehicles, such as passenger cars, buses, long-distance buses, trucks, subways, railways, planes, and various places and facilities such as elevators, air conditioners, and cold storage. The device is instrumental in disinfecting the COVID-19. It is noted that the device can be installed in air conditioning systems, such as an air inlet, an air outlet or a ventilation pipe, so as to kill the COVID-19 and adjust the air temperature.

BRIEF DESCRIPTION OF DRAWINGS

FIG. 1 is a three-dimensional structure diagram of an air sterilization device with a heating apparatus.

FIG. 1-1 is an A-A section view of FIG. 1.

FIG. 2 is a three-dimensional structure diagram of an air sterilization device with heating apparatus and water bath.

FIG. 2-1 is a front view of FIG. 2.

FIG. 2-2 is a B-B section view of FIG. 2-2.

FIG. 2-3 is a C-C section view of FIG. 2-2.

FIG. 3 is a three-dimensional structure diagram of an air sterilization device with heating apparatus and water bath with a thermostat.

FIG. 3-1 is a D-D section view of FIG. 3.

FIG. 4 is a three-dimensional structure diagram of an air sterilization device with heating apparatus and water curtain.

FIG. 5 is a three-dimensional structure diagram of an air sterilization device with heating apparatus and cooling apparatus.

FIG. 5-1 is an E-E section view of FIG. 5.

FIG. 5-2 is an amplified drawing of the F region of FIG. 5-1.

FIG. 6 is a three-dimensional structure diagram of a mainframe with two-stage fan of an air sterilization device with heating apparatus.

FIG. 6-1 is an amplified drawing of the G of FIG. 6.

FIG. 7 is a three-dimensional structure diagram of a two-stage fan.

FIG. 7-1 is an exploded view of the two-stage fan of FIG. 7.

FIG. 8 is a three-dimensional structure diagram of a heating coil distributed longitudinally along the direction of air flow.

In the foregoing accompanying drawings:

100 is an air sterilization device with heating apparatus, 101 is a centrifugal machine.

1 is a mainframe, 2 is a sterilization system, 3 is a heating system, 4 is circuits and a control system, 5 is a housing, 6 is an air filtration apparatus, 7 is a water filtration apparatus, 8 is an air booster pump, and 9 is a cooling device.

11 is an air inlet unit, 12 is an exhaust unit, 13 is an exhaust pipe, 14 is a motor, 15 is a rotating shaft, 16 is a first-stage blade, 17 is a second-stage blade, 18 is a permanent seat, 19 is a protective cap, 21 is ultraviolet sterilization apparatus, 31 is a heating rod, 32 is a heating plate, 33 is a heating coil, 41 is a control panel, 51 is an air inlet 52 is an air outlet, 71 is a water curtain, 72 is a water bath, 91 is a heat conduction cooling plate.

21-1 is an ultraviolet disinfection chamber, 33-1 is a heating wire, 72-1 is a thermostat, 72-11 is a heating unit, 72-12 is a temperature setting switch, 91-1 is a cooling surface, and 91-2 is a heat delivery surface.

DETAILED DESCRIPTION

Embodiment 1: An Air Sterilization Device with Heating Apparatus

Referring to FIG. 1 and FIG. 1-1, the specific part drawings designed according to the technical solutions of the present application are shown.

An air sterilization device with a heating apparatus comprises mainframe 1, sterilization system 2, heating system 3, circuits and control system 4 and housing 5.

In this embodiment, the mainframe 1 is a centrifugal machine which includes air inlet unit 11 and exhaust unit 12. When the centrifugal machine 101 works, air is drawn in from the air inlet unit 11 by the centrifugal machine 101 and then discharged through the exhaust unit 12. The air circulates between the room and the housing 5.

The sterilization system 2 is an ultraviolet sterilization apparatus 21 that can sterilize and disinfect air.

The heating system 3 can heat the air to inactivate viruses. The temperature heated by the heating system 3 should no less than 56° C. and normally it can be set at 60° C. In most cases, capsid proteins of viruses denaturates at 55-60° C.

within several minutes, rendering the virus incapacitated. Thus, the temperature heated by the heating system 3 should be at above 56° C. or 60° C. to better inactivate viruses. At the same time, the ozone will be decomposed quickly in the course of sterilization and disinfection by the ultraviolet sterilization apparatus 21 when it is at above 50° C., in a bid to avoid the ozone produced in the sterilization process to cause secondary pollution to the air.

Referring to FIG. 1-1, in this embodiment, the heating system 3 is heating coil 33 which can heat the air and keep better heating effect. In practice, the heating system 3 can serve as the heating rod 31 or heating plate 32, or a combination of several heating methods. It also will be understood by those of ordinary skill or technology in the art there various changes in form and details may be made therein without departing from the spirit and scope of the present application.

The mainframe 1, the ultraviolet sterilization apparatus 21 and the heating system 3 can connect power source through the circuits and control system 4.

The circuits and control system 4 can control the opening and closing of the mainframe 1 and the ultraviolet sterilization apparatus 21. The time of duration and the intensity of ultraviolet irradiation of the ultraviolet sterilization apparatus 21 can be set and adjusted by the circuits and control system 4 and the control panel 41. The heating temperature and heating duration of the heating system 3 can be set and adjusted by the circuits and control system 4 and the control panel 41.

The housing 5 consists of air inlet 51 and air outlet 52. In this embodiment, the air inlet 51 is located in the bottom of the housing 5 and the air outlet 52 on the top of the housing 5.

In this embodiment, the inner side of the upper part of the housing 5 is made of mirror stainless steel that is resistant to ultraviolet ray. The upper part of the housing 5 constitutes the ultraviolet disinfection chamber 21-1 in which the ultraviolet sterilization apparatus 21 and the heating coil 33 are installed. The ultraviolet sterilization apparatus 21 is installed in the ultraviolet disinfection chamber 21-1. Ultraviolet disinfection utilizes appropriate wavelength of ultraviolet to destroy DNA or RNA molecular structure of microbial body cells, resulting in growth cell death and/or regenerative cell death, to achieve the effect of sterilization and disinfection. Thus, the ultraviolet may cause accidental harm to human body, if poorly protected in the course of sterilization. In order to avoid accidental harm to human body, it is imperative to install the ultraviolet sterilization apparatus 21 in the ultraviolet disinfection chamber 21-1.

Mirror stainless steel is the material that can reflect ultraviolet rays, in order to ensure the isolation effect at the same time, and enhance the ultraviolet intensity in the ultraviolet disinfection chamber 21-1, and the sterilization effect is better. In order to further strengthen the sterilization effect, multiple ultraviolet sterilization apparatus 21, such as ultraviolet lamps, can be uniformly distributed around the ultraviolet disinfection chamber 21-1 to ensure the uniform distribution of ultraviolet rays in the ultraviolet disinfection chamber 21-1, so as to ensure the sterilization effect.

Referring to FIG. 1-1, in this embodiment, the air sterilization device 100 with the heating apparatus includes the air filtration apparatus 6 that can filter dust particles, odor, toxic gases and other air pollutants in the air.

The air filtration apparatus 6 is made of ceramic materials which can be heated to at above 56° C. by the heating system 3. But the optimum temperature is at 70° C. to 150° C. The air passes through heated ceramic materials to kill bacteria and viruses. The air filtration apparatus 6 can be replaced regularly, which is safer and more sanitary, which can quickly kill bacteria and viruses attached to the ceramic materials at high temperature and which can improve the efficiency of air sterilization and disinfection.

In practice, the centrifugal machine 101 works after it is powered and turned on. Air enters in the housing 5 through the air inlet 51 and then flows into the mainframe 1 through the air filtration apparatus 6 and the air inlet unit 11. The air is discharged through the exhaust unit 12 and enters into the ultraviolet disinfection chamber 21-1 through the exhaust pipe 13. And then, the ultraviolet disinfection chamber 21-1 disinfects the air that is heated by the heating system 3 to inactivate the viruses in the sterilized air and decompose the ozone produced in the course of ultraviolet disinfection quickly. In the end, the air is discharged into the room from the air outlet 52 by way of the exhaust pipe 13.

To ensure the inactivated effect on viruses and other microorganisms, the heating system 3 should be heated to above 60° C. that can decompose the ozone produced in the course of sterilization and disinfection by the ultraviolet sterilization apparatus 21 into oxygen, further effectively avoid secondary pollution to the air and better disinfect and purify the air.

In this embodiment, the air sterilization device with heating apparatus can heat the air to inactivate viruses twice and decompose the ozone produced in the course of sterilization and disinfection by the ultraviolet sterilization apparatus 21 and the heating system 3 to avoid secondary pollution to the air and better purify the air.

Figure 2:
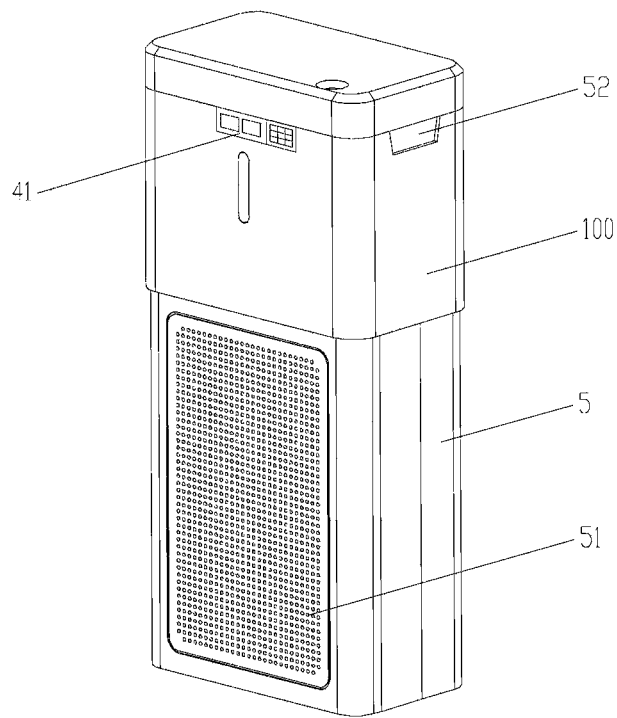
Figures 1, 2:
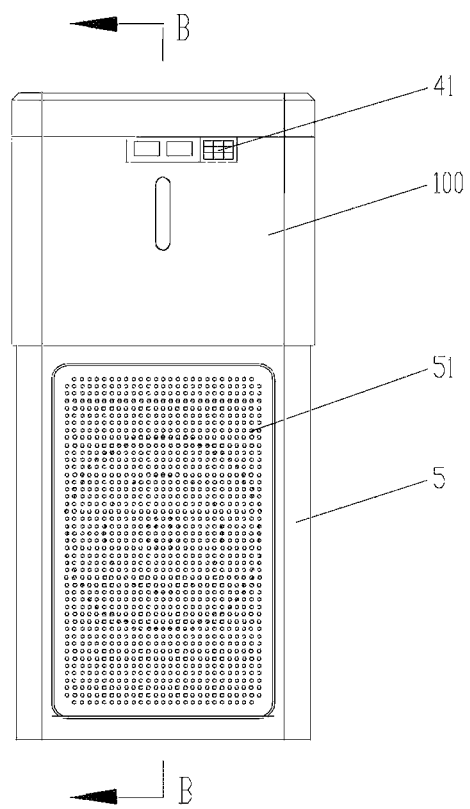
Figure 2:
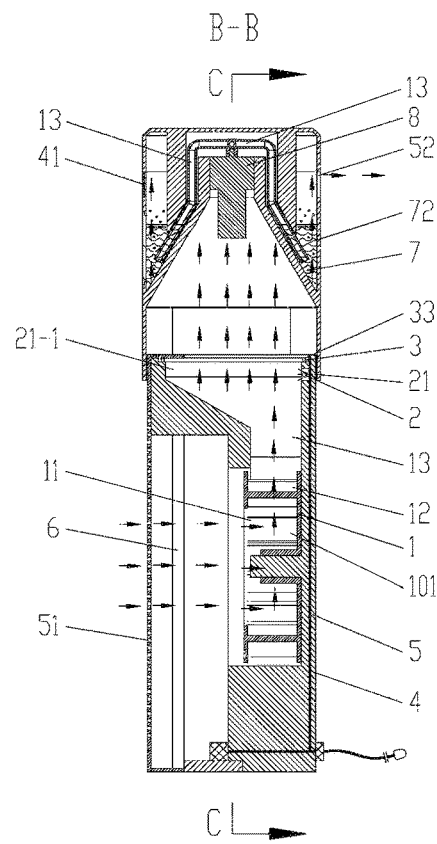
Figures 2, 3:
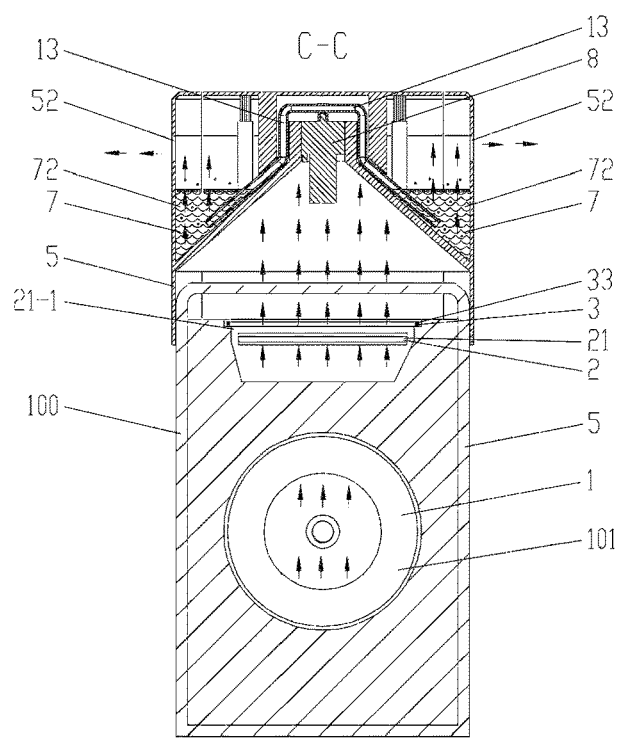
Figure 3:
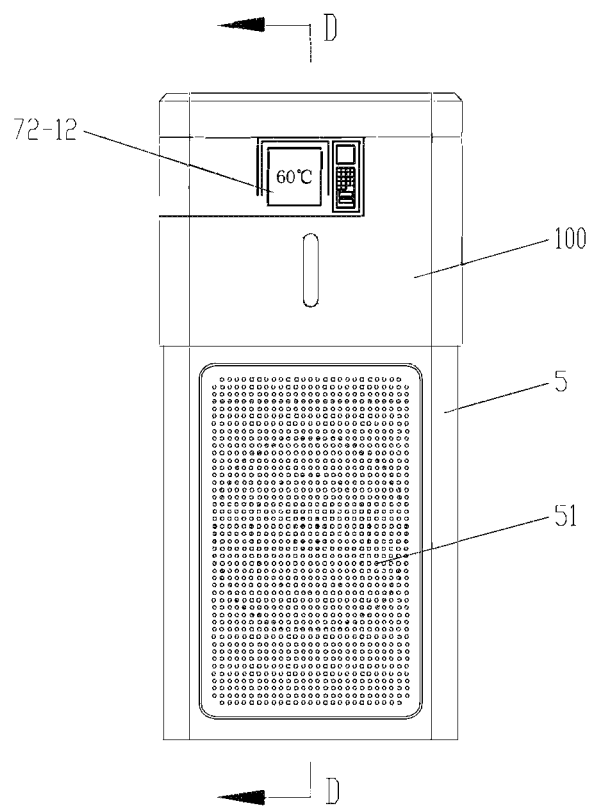
Figures 1, 3:
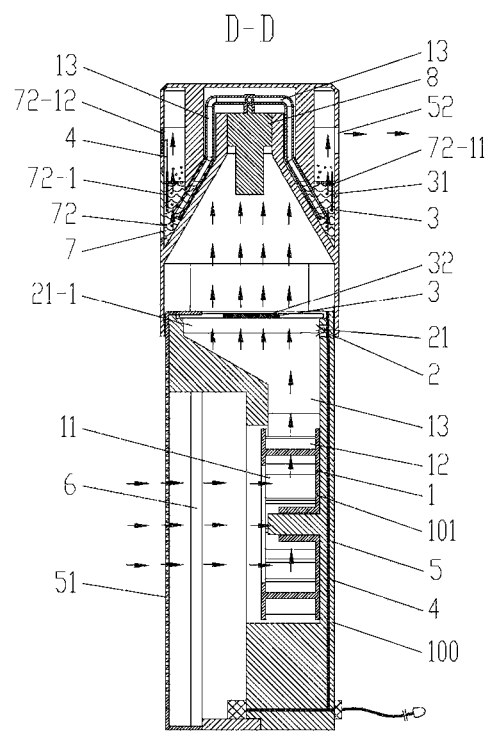
Figure 4:
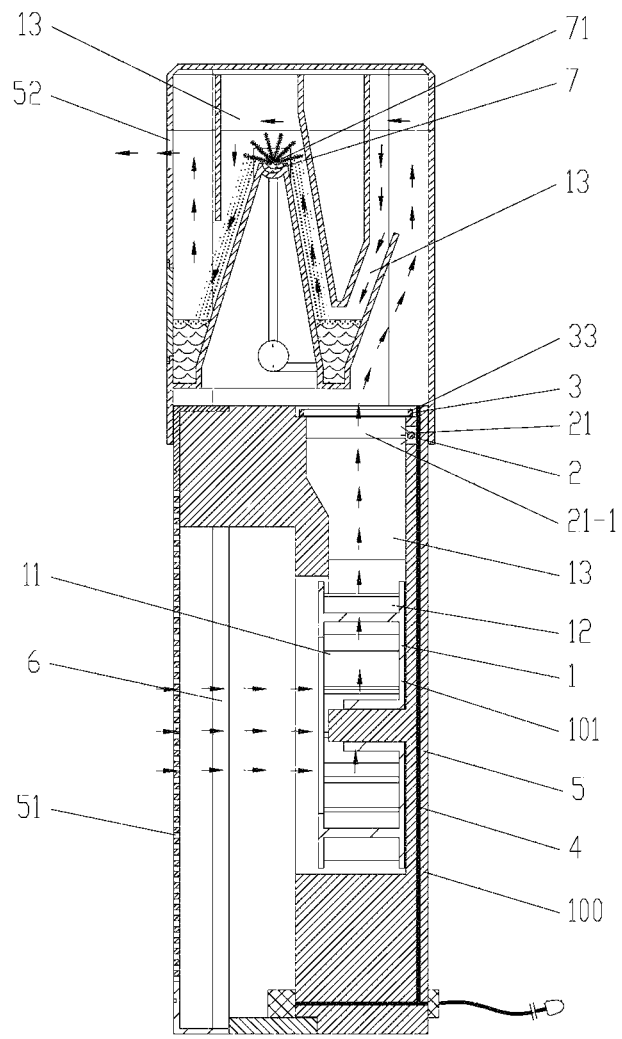
Figure 5:
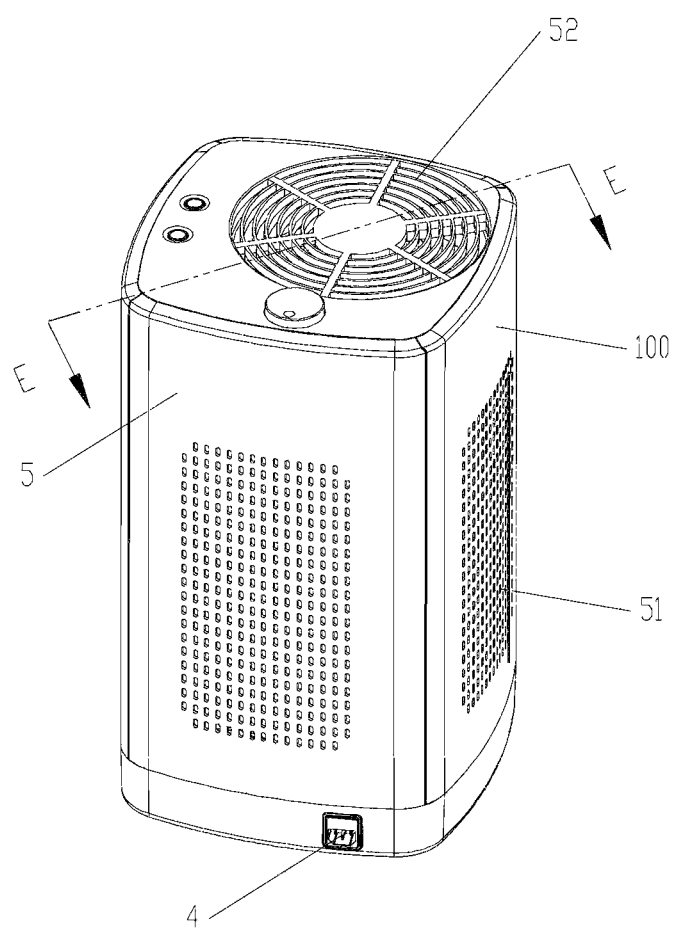
Figures 1, 5:
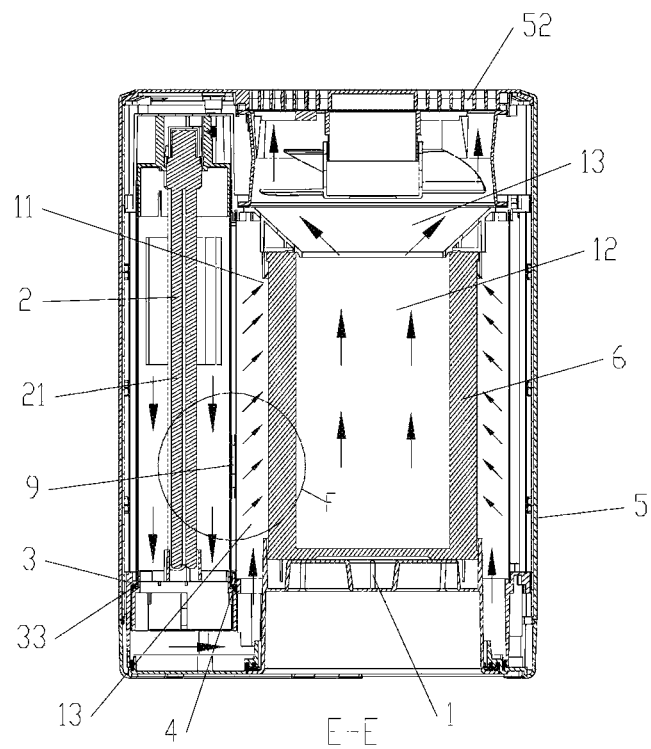
Figures 2, 5:
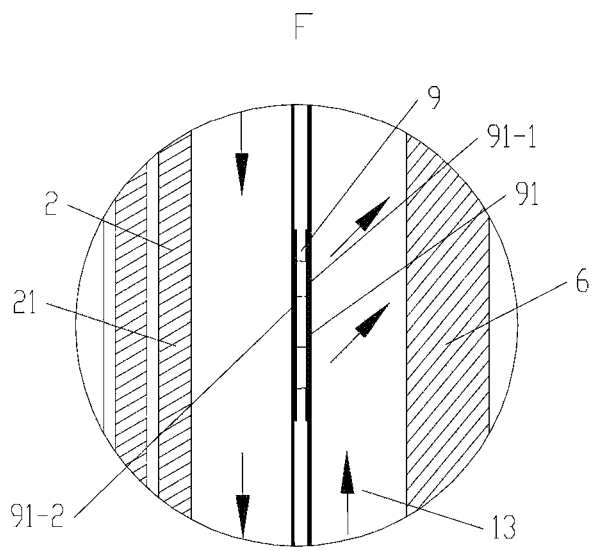

Embodiment 2: an Air Sterilization Device with Heating Apparatus is Installed Water Filtration Apparatus Referring to FIG. 2 to FIG. 4, technical principles of this embodiment are similar to those in embodiment 1, and the difference only lies in that: the air sterilization device with heating apparatus also comprises water filtration apparatus 7.

The water filtration apparatus 7 could be water curtain 71 or water bath 72.

Referring to FIG. 4, the water curtain 71 has such a simple structure, but it cannot be set constant temperature.

Referring to FIG. 2 and FIG. 2-1, in this embodiment, the water filtration apparatus 7 is water bath 72.

The air booster pump 8 is installed exhaust pipe 13 in the front of the water bath 72, which can increase air pressure, so as to ensure that the sterilized air flows into the water bath 72. And then the air is discharged after the motion of liquid in the water bath 72 screens the air motion.

Referring to FIG. 3 and FIG. 3-1, the water bath 72 is installed thermostat 72-1, which can keep the liquid in the water bath 72 at a constant temperature. And according to different needs, different temperature can be set by the temperature setting switch 72-12, so as to better inactivate viruses.

Referring to FIG. 3-1, the heating unit 72-11 in the thermostat 72-1 comprises the heating rod 31. The air sterilized by ultraviolet rays flows into the water bath 72 through air pipelines and the liquid in the water bath 72 can be heated by the heating unit 72-11. The liquid heated can inactivate the viruses in the air sterilized by ultraviolet rays, and decompose the ozone produced in the course of ultraviolet disinfection. And at the same time, the air flows into the room in a gentle manner, reducing air fluctuation.

In this embodiment, the heating system 3 includes the heating plate 32 sited on the upper part of the ultraviolet sterilization apparatus 21, except the heating rod 31 in the water bath 72. The heating plate 32 can heat the air sterilized by the ultraviolet sterilization apparatus 21, so as to inactivate the viruses in the air, and at the same time to accelerate the decomposition of the ozone produced in the course of sterilization and disinfection by the ultraviolet sterilization apparatus 21.

The heating temperature of the heating system 3 can be set by the temperature setting switch 72-12 according to types of infectious viruses in different seasons. In practice, when the mainframe 1 is powered and the switch is on, air enters in the housing 5 through the air inlet 51. The air enters into the mainframe 1 through the air inlet unit 11 after it is filtered by the air filtration apparatus 6. The air is discharged through the exhaust unit 12 and enters into the ultraviolet disinfection chamber 21-1 through the exhaust pipe 13. And then, the ultraviolet sterilization apparatus 21 disinfects the air filtered and the heating plate 32 in the ultraviolet sterilization apparatus 21 heats the air to inactivate viruses in the air and decomposes the ozone produced in the course of ultraviolet disinfection in a quick manner. The sterilized air enters in the water bath 72 by the exhaust pipe 13. The liquid in the water bath 72 is heated by the heating rod 31 and can reduce moving rate of the air to further inactivate the possible residual viruses and decompose the residual ozone. The air is discharged gently into the room through the air outlet 52, avoiding causing fluctuations in surrounding air.

In this embodiment, the air sterilization device 100 with heating apparatus includes water filtration apparatus 7, so as to avoid large fluctuations in surrounding air when the air is discharged into the room. Because viruses usually requires a carrier to spread, the greater the air fluctuates and the faster the viruses spread. The water filtration apparatus 7 can reduce the fluctuation of the sterilized and disinfected air, so that the air can be discharged into room, avoiding large fluctuations in surrounding air, in a bid to slow down the movement of the viral vectors and the speed of viruses.

Embodiment 3: an Air Sterilization Device with Heating Apparatus is Installed Cooling Apparatus Referring to FIG. 5 and FIG. 5-2, the difference between embodiment 3 and embodiment 1 lies in that the air sterilization device 100 with heating apparatus includes cooling apparatus 9.

In this embodiment, the cooling apparatus 9 is the heat conduction cooling plate 91, which is made of thermoelectric ceramics that include a cooling surface 91-1 and a heat delivery surface 91-2. The cooling surface 91-1 is installed on the side toward the exhaust pipe 13 and can cool the air, and the heat delivery surface 91-2 on the side toward the ultraviolet sterilization apparatus 21 which conducts heat into the ultraviolet disinfection chamber 21-1. The air passes through the cooling surface 91-1, which works to reduce the temperature of the air to a safe temperature to prevent the air filtration apparatus 6 from being damaged by high air temperature or to prevent accidental damage. The heat delivery surface 91-2 conducts the heat generated in the process of reducing air temperature to the side of the ultraviolet sterilization apparatus 21 and assists heating system 3 to heat the air disinfected by the ultraviolet sterilization apparatus 21.

In practice, the cooling apparatus 9 may be a cold rinse bank, cold water pipes or other cooling apparatus. It also will be understood by those of ordinary skill or technology in the art there various changes in form and details may be made therein without departing from the spirit and scope of the present application.

In this embodiment, the air sterilization device 100 comprises mainframe 1, sterilization system 2, heating system 3, circuits and control system 4, housing 5, air filtration apparatus 6 and cooling apparatus 9.

The mainframe 1 is the centrifugal machine 101 which includes air inlet unit 11 and exhaust unit 12. When the centrifugal machine 101 works, air is drawn in from the air inlet unit 11 by the centrifugal machine 101 and then discharged through the exhaust unit 12. The air circulates between the room and the housing 5.

The sterilization system 2 is the ultraviolet sterilization apparatus 21 that can sterilize and disinfect air. The ultraviolet sterilization apparatus 21 is installed in the ultraviolet disinfection chamber 21-1.

The heating system 3 is the heating coil 33 under the ultraviolet sterilization apparatus 21. The heating coil 33 can heat the air sterilized and disinfected by the ultraviolet sterilization apparatus 21, so as to inactivate the viruses. And at the same time, the ozone produced in the course of sterilization and disinfection by the ultraviolet sterilization apparatus 21 can be decomposed quickly when the temperature is at above 50° C., in order to avoid secondary pollution to air.

After the air heated by the heating coil 33 is cooled by the cooling apparatus 9 through exhaust pipe 13, the air enters in the mainframe 1 through the air filtration apparatus 6 and the air inlet unit 11 respectively and is discharged into the room through the exhaust unit 12.

In this embodiment, the air sterilization device with heating apparatus is installed cooling apparatus 9, which reduces the air temperature to a safe temperature and then discharges the air into the room, so as to keep the air filtration apparatus 6 from being damaged by high temperature and ensure that the air flowing into the room is safe in temperature. In addition, the air is first sterilized and disinfected and then filtered by the air filtration apparatus 6, which can ensure that no virus is attached to the air filtration apparatus 6, and that the process of replacing and cleaning the air filtration apparatus 6 is safer.

Embodiment 4: an Air Sterilization Device with Heating Apparatus Comprises Two-Stage Fan Referring to FIG. 6 to FIG. 8, the difference between embodiment 4 and embodiment 3 lies in that the mainframe 1 of the air sterilization device 100 is two-stage fan 102.

Referring to FIG. 7 and FIG. 7-1, the two-stage fan 102 comprises motor 14, rotating shaft 15, first stage blade 16, second stage blade 17 and permanent seat 18.

The motor 14 connects to the first-stage blade 16 and the second-stage blade 17 by the rotating shaft 15; the motor 14 is installed in the permanent seat 18; the motor 14 drives the first stage blade 16 and the second stage blade 17 to rotate by the rotating shaft 15, the Circuits 4 and Control System 4.

In this embodiment, the two-stage fan 102 has protective cap 19 in which the motor 14, the rotating shaft 15, the first stage blade 16, the second stage blade 17 and the permanent seat 18 are assembled and installed.

The first stage blade 16 is smaller than the second stage blade 17 in size, which can discharge the sterilized and purified air into the room in an efficient and quick way.

Referring to FIG. 8, in this embodiment, the heating apparatus is a heating coil 33. The heating coil 33 is wound by a heating wire 33-1 along the direction of air flow and distributed longitudinally. This winding method along the direction of air flow can maximize the width of air heating distance, kill viruses and decompose ozone better.

The cooling apparatus 9 is heat conduction cooling plate 91 arranged in many places along the direction of air flow.

Figure 6:
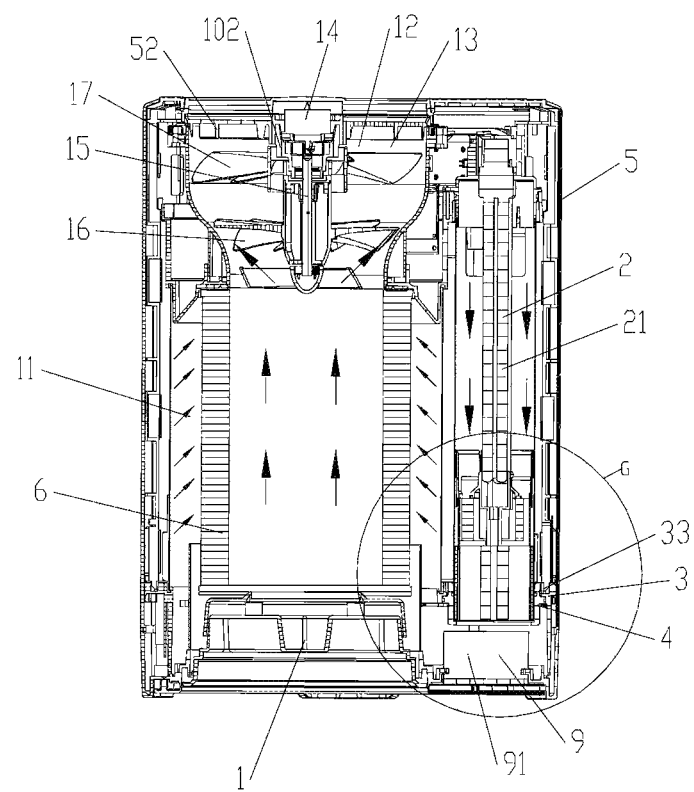
Figures 1, 6:
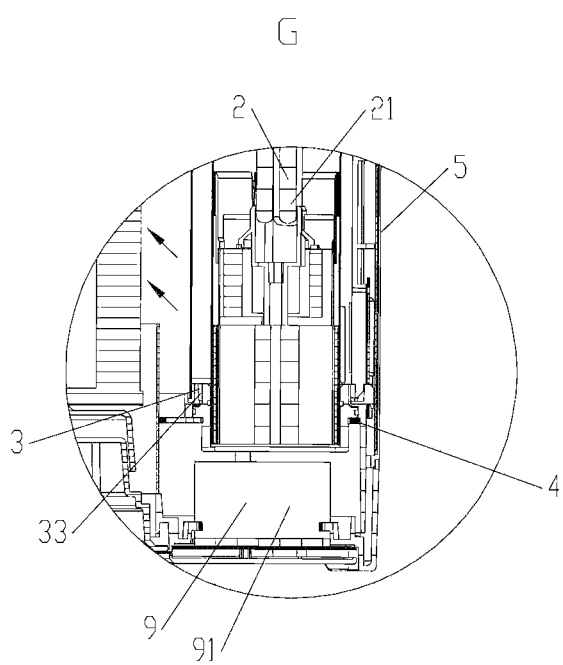
Figure 7:
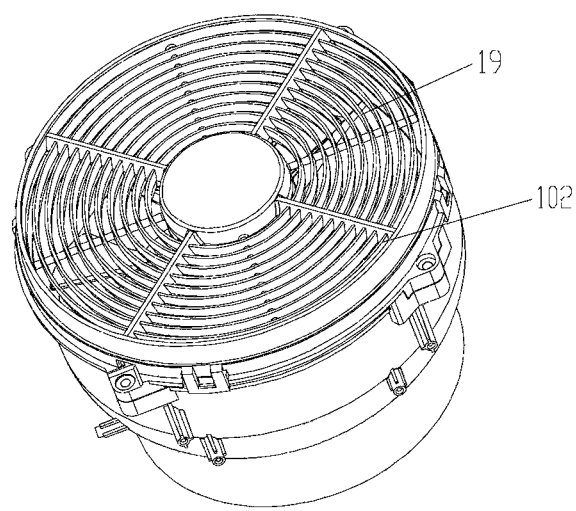
Figures 1, 7:
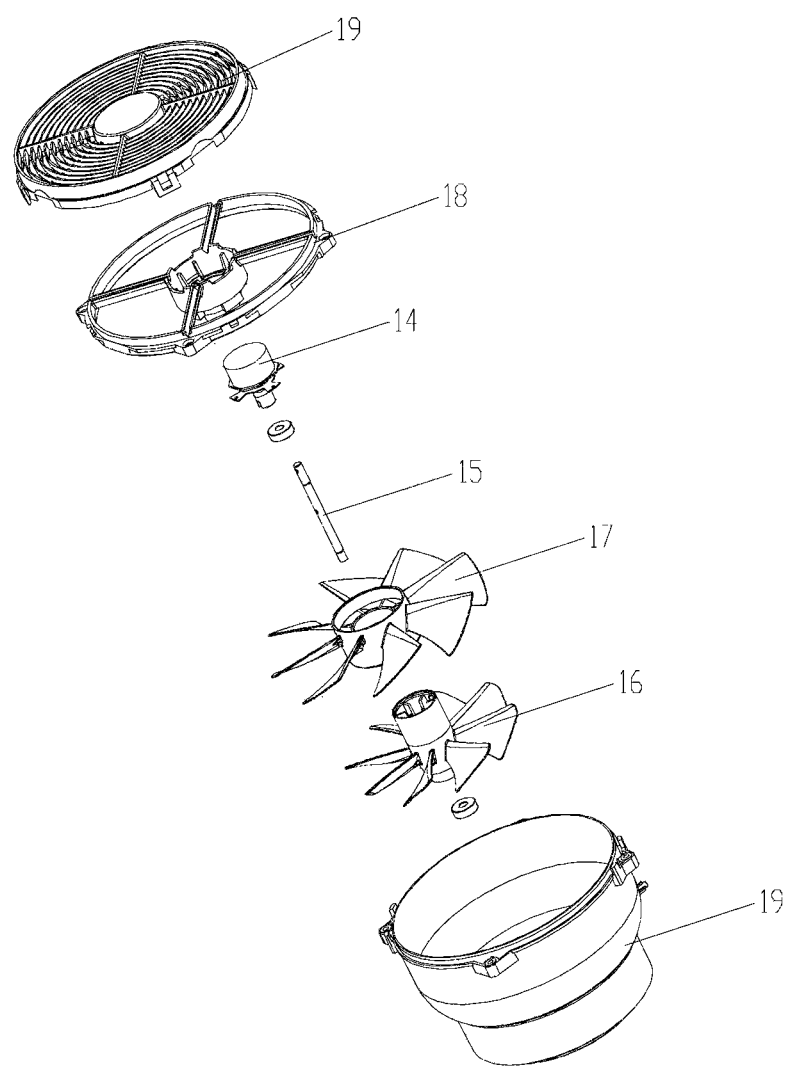
Figure 8:
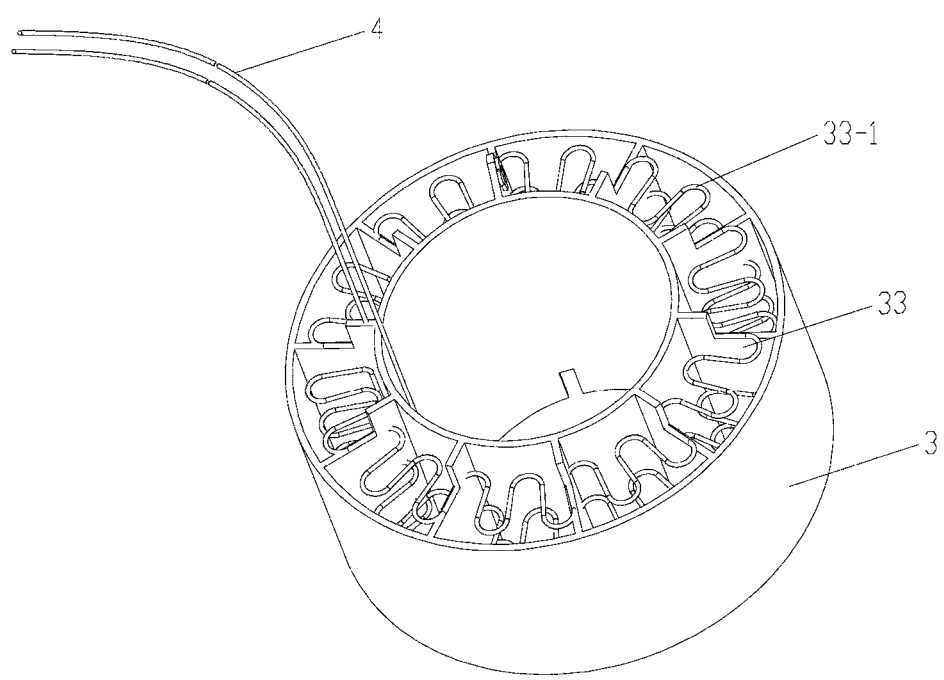

Referring to FIG. 6, in practice, the air to be disinfected and purified enters the housing 5 through the air inlet 51 and is sterilized and disinfected by the ultraviolet sterilization apparatus 21. Going forward, the air needs further sterilization and disinfection by the heating coil 33, which decomposes the ozone produced in the course of sterilization and disinfection. And then, the sterilized and disinfected air is cooled by the cooling apparatus 9 and discharged into the room through the air filtration apparatus 6, by the two-stage fan 102.

In this embodiment, because the mainframe 1 is two-stage fan 102, the air volume is larger than ordinary centrifuge, thus the effect of air disinfection and sterilization is better.

It should be noted that the structures disclosed and described herein may be replaced by other structures with the same effect, and meanwhile, the embodiments introduced in the present application are not the unique structures implementing the present application. Although preferred embodiments of the present application are already introduced and described in the specification, it is clearly known by persons of skill in the art that the embodiments are merely examples, and persons of skill in the art can make innumerable change, improvement and replacement without departing from the present application. Therefore, the protection scope of the present application shall be limited according to the spirit and scope of claims accompanied by the present application.

What is claimed is:

1. An air sterilization device with heating apparatus, comprising a mainframe, a sterilization system, a heating system, circuits and a control system and a housing, wherein:
   the sterilization system includes an ultraviolet sterilization apparatus that is configured to sterilize and disinfect air;
   the heating system is configured to heat the air to inactivate virus in the air;
   the housing comprises an air inlet and an air outlet;
   the mainframe, the ultraviolet sterilization apparatus and the heating system are powered through the circuits and the control system;
   the ultraviolet sterilization apparatus and the heating system are installed in the housing; and
   the mainframe is configured to cause the air to flow into the housing through the air inlet and be discharged from the air outlet into a room after the air is sterilized and disinfected by the ultraviolet sterilization apparatus and the heating system.

2. The air sterilization device with heating apparatus according to claim 1, wherein the heating system is configured to eliminate ozone generated by the ultraviolet sterilization apparatus to reduce the ozone level of the air discharged into the room.

3. The air sterilization device with heating apparatus according to claim 1, wherein the mainframe is a centrifugal machine which includes an air inlet unit and an exhaust unit.

4. The air sterilization device with heating apparatus according to claim 1, wherein the mainframe is a two-stage fan which includes a motor, a rotating shaft, a first-stage blade, a second-stage blade and a permanent seat.

5. The air sterilization device with heating apparatus according to claim 4, wherein the motor connects to the first-stage blade and the second-stage blade by the rotating shaft; the motor is installed in the permanent seat; and the motor drives the first-stage blade and the second-stage blade to rotate by the rotating shaft and the circuits and the control system.

6. The air sterilization device with heating apparatus according to claim 4, wherein the two-stage fan has a protective cap.

7. The air sterilization device with heating apparatus according to claim 4, wherein the first-stage blade is smaller than the second-stage blade in size.

8. The air sterilization device with heating apparatus according to claim 1, wherein the heating system is one of a heating rod, a heating plate, and/or a heating coil.

9. The air sterilization device with heating apparatus according to claim 8, wherein the heating coil is wound by a heating wire along a direction of air flow and distributed longitudinally.

10. The air sterilization device with heating apparatus according to claim 1, wherein the ultraviolet sterilization apparatus is installed in an ultraviolet disinfection chamber.

11. The air sterilization device with heating apparatus according to claim 10, wherein the ultraviolet disinfection chamber is made of a material resistant to ultraviolet rays and leakage of ultraviolet rays.

12. The air sterilization device with heating apparatus according to claim 10, wherein the ultraviolet disinfection chamber is made of a minor-surface stainless steel that can reflect ultraviolet rays, or a mirror-surface polymer material that are resistant to ultraviolet radiation.

13. The air sterilization device with heating apparatus according to claim 1, wherein the air is configured to flow into the housing through the air inlet and is discharged from the air outlet into a room after the ultraviolet sterilization apparatus first sterilizes and disinfects the air and the heating system heats the air.

14. The air sterilization device with heating apparatus according to claim 1, wherein the heating system and the ultraviolet sterilization apparatus are integrated into one piece.

15. The air sterilization device with heating apparatus according to claim 14, wherein the ultraviolet sterilization apparatus sterilizes the air in the ultraviolet disinfection chamber and the heating system heats the air sterilized by the ultraviolet sterilization apparatus simultaneously.

16. The air sterilization device with heating apparatus according to claim 1, wherein the air sterilization device with heating apparatus comprises an air filtration apparatus.

17. The air sterilization device with heating apparatus according to claim 1, wherein the air sterilization device with heating apparatus comprises a water filtration apparatus.

18. The air sterilization device with heating apparatus according to claim 17, wherein the water filtration apparatus is a water curtain or a water bath.

19. The air sterilization device with heating apparatus according to claim 18, wherein an air booster pump is installed in the exhaust pipe in the front of the water bath.

20. The air sterilization device with heating apparatus according to claim 1, wherein the air sterilization device with heating apparatus comprises a cooling device.

* * * * *